United States Patent [19]

Coates et al.

[11] Patent Number: 4,946,842
[45] Date of Patent: Aug. 7, 1990

[54] NOVEL GUANIDINO PYRIDAZINONES AS CARDIAC STIMULANTS

[75] Inventors: William J. Coates, Welwyn Garden City; John C. Emmett, Welwyn; Robert A. Slater, Letchworth, all of England

[73] Assignee: Smith Kline & French Laboratories Limited, Welwyn Garden City, England

[21] Appl. No.: 880,372

[22] Filed: Jun. 30, 1986

[30] Foreign Application Priority Data

Jul. 5, 1985 [GB] United Kingdom ............... 8517052
Jul. 5, 1985 [GB] United Kingdom ............... 8517053
Jul. 5, 1985 [GB] United Kingdom ............... 8517054
Jul. 5, 1985 [GB] United Kingdom ............... 8517055

[51] Int. Cl.$^5$ ............... C07D 237/04; C07D 401/12; C07D 403/12; A61K 31/50
[52] U.S. Cl. ............... 514/247; 514/252; 514/253; 544/238; 544/239
[58] Field of Search ............... 544/235, 239, 238; 514/247, 252, 253; 564/103, 104

[56] References Cited

U.S. PATENT DOCUMENTS

| 4,171,325 | 10/1979 | Brown et al. | 564/104 |
| 4,279,911 | 7/1981 | Martin-Smith et al. | 424/251 |
| 4,317,819 | 3/1982 | Clitherow et al. | 424/244 |
| 4,332,822 | 6/1982 | Ward | 424/324 |
| 4,491,595 | 1/1985 | Niemers et al. | 424/326 |
| 4,544,562 | 10/1985 | Rossy et al. | 514/247 |
| 4,654,342 | 3/1987 | Slater | 514/247 |

FOREIGN PATENT DOCUMENTS 0150937 11/1985 European Pat. Off. .

OTHER PUBLICATIONS

Curran et al., J. Medicinal Chemistry, 17, p. 273 (1974).

Primary Examiner—Mark L. Berch
Attorney, Agent, or Firm—Charles M. Kinzig; Stuart R. Suter; Edward T. Lentz

[57] ABSTRACT

The invention relates to phenyl dihydropyridazinone derivatives that have utility as cardiac stimulants. A compound of the invention is 6-[4-($N^3$-benzyl-$N^2$-cyanoguanidino)phenyl]-5-methyl-4,5-dihydro-3(2H)-pyridazinone.

20 Claims, No Drawings

GUANIDINO PYRIDAZINONES AS CARDIAC STIMULANTS

The present invention relates to dihydropyridazinone derivatives and in particular to such compounds having a substituted phenyl group at the 6-position of the dihydropyridazinone ring. This invention further relates to pharmaceutical compositions containing them and a method of stimulating cardiac activity by administering them. The compounds of this invention are phosphodiesterase type III inhibitors and are of use in combatting such conditions wherein such inhibition is thought to be beneficial. Thus the compounds of this invention are positive inotropic agents and vasodilators and are therefore of value in combatting cardiovascular disease, in particular congestive heart failure. In addition the compounds of this invention inhibit platelet aggregation and therefore have an antithrombotic effect. Furthermore the compounds of this invention are bronchodilators and are therefore of use in combatting chronic obstructive lung diseases such as asthma and bronchitis. The major utility of the compounds of this invention is in the treatment of congestive heart failure, for such treatment the compounds have a very desirable profile of activity.

Congestive heart failure is traditionally treated with cardiac glycosides, for example digoxin and digitoxin, and sympathomimetic agents. The glycosides have pronounced toxic effects with a low therapeutic index. The sympathomimetic agents generally do not have the desired profile of activity and are not orally effective. Amrinone is a marketed compound of interest that is reported to be an inotropic agent. This has an undesirable profile of side-effects when administered orally and currently development is being restricted to other modes of administration. Clearly there is a continuing need for orally active inotropic agents that have a good therapeutic profile.

Accordingly the present invention provides compounds of the formula (I):

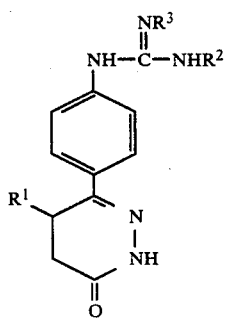

and pharmaceutically acceptable salts thereof, wherein
R$^1$ is hydrogen or methyl,
R$^2$ is C$_{1-4}$alkyl, substituted by one or two groups selected from hydroxy, C$_{1-4}$alkoxy, carbamoyl, C$_{1-4}$alkoxycarbonyl and trifluoromethy, provided that the carbon atom adjacent to the nitrogen atom is not substituted by hydroxy and that no carbon atom is disubstituted by hydroxy, or —A—R$^4$ where A is C$_{1-4}$alkylene (straight or branched) and R$^4$ is optionally substituted aryl or heteroaryl,
R$^3$ is cyano, —COR$^5$ or —SO$_2$R$^6$ where R$^5$ is C$_{1-4}$alkyl, C$_{1-4}$ alkoxy or optionally substituted phenyl and R$^6$ is NHR$^7$, C$_{1-4}$alkyl or optionally substituted aryl; and R$^7$ is hydrogen or C$_{1-4}$alkyl,
R$^2$ can also be C$_{3-6}$cycloalkyl, allyl or propargyl when R$^3$ is cyano, and
R$^2$ can also be hydrogen or C$_{1-4}$alkyl when R$^3$ is —COR$^5$ or —SO$_2$R$^6$.

Examples of C$_{1-4}$alkyl are methyl, ethyl, n-propyl, isopropyl, n-butyl, isobutyl, sec-butyl and tert-butyl. Examples of C$_{1-4}$alkoxy are methoxy, ethoxy, n-propoxy, n-butoxy and tert-butoxy. Examples of C$_{1-4}$alkoxycarbonyl are methoxycarbonyl, ethoxycarbonyl, n-propoxycarbonyl, n-butoxycarbonyl and tert-butoxycarbonyl. Examples of C$_{1-4}$alkylene are methylene, 1,2-ethanediyl, 1,3-propanediyl, 1,2-propanediyl and 1,4-butanediyl. Examples of C$_{3-6}$cycloalkyl are cyclopropyl, cyclobutyl, cyclopentyl or cyclohexyl.

Preferably R$^1$ is methyl.
Preferably R$^2$ is 2-hydroxyethyl or 2-methoxyethyl.
Preferably A is CH$_2$ or CH$_2$CH$_2$.
Suitably R$^4$ is phenyl optionally substituted by one or two alkoxy, halo, hydroxy, sulphonamido, or trifluoromethyl groups, or is 2,3 or 4-pyridyl or 2-benzimidazolyl.
Preferably R$^4$ is phenyl, 4-hydroxyphenyl or 2-pyridyl.
Preferably R$^2$ is benzyl or 4-hydroxybenzyl.
Suitably R$^3$ is cyano.
Suitably R$^3$ is acetyl, methylsulphonyl or phenylsulphonyl.
Suitably R$^2$ is cyclopropyl, allyl or propargyl and R$^3$ is cyano.
Suitably R$^2$ is hydrogen or methyl and R$^3$ is acetyl, methylsulphonyl or phenylsulphonyl.
Preferably R$^2$ is methyl and R$^3$ is methylsulphonyl or phenylsulphonyl.

Particular compounds of this invention are:
6-[4-(N$^2$-acetylguanidino)phenyl]-5-methyl-4,5-dihydro(3(2H)-pyridazinone,
6-[4-(N$^3$-methyl-N$^2$-methylsulphonylguanidino)-phenyl]-5-methyl-4,5-dihydro-3(2H)-pyridazinone,
6-[4-(N$^3$-methyl-N$^2$-phenylsulphonylguanidino)-phenyl]-5-methyl-4,5-dihydro-3(2H)-pyridazinone,
6-[4-(N$^3$-(2-methoxyethyl)-N$^2$-cyanoguanidino)-phenyl]-5-methyl-4,5-dihydro-3(2H)-pyridazinone
6-[4-(N$^3$-(2-hydroxyethyl)-N$^2$-cyanoguanidino)-phenyl]-5-methyl-4,5-dihydro-3(2H)-pyridazinone,
6-[4-(N$^3$-cyclopropyl-N$^2$-cyanoguanidino)phenyl]-5-methyl 4,5-dihydro-3(2H)-pyridazinone,
6-[4-(N$^3$-allyl-N$^2$-cyanoguanidino)phenyl]-5-methyl-4,5-dihydro-3(2H)-pyridazinone,
6-[4-(N$^3$-propargyl-N$^2$-cyanoguanidino)phenyl]-5-methyl-4,5-dihydro-3(2H)-pyridazinone,
6-[4-(N$^3$-(4-hydroxybenzyl)-N$^2$-cyanoguanidino)-phenyl]-5-methyl-4,5-dihydro-3(2H)-pyridazinone,
6-[4-(N$^3$-benzyl-N$^2$-cyanoguanidino)phenyl]-5-methyl-4,5-dihydro-3(2H)-pyridazinone,
6-[4-(N$^3$-(4-methoxybenzyl)-N$^2$-cyanoguanidino)-phenyl]-5-methyl-4,5-dihydro-3(2H)-pyridazinone,
6-[4-(N$^3$-(2-pyridylmethyl)-N$^2$-cyanoguanidino)-phenyl]-5-methyl-4,5-dihydro-3(2H)-pyridazinone, and
6-[4-(N$^3$-phenethyl-N$^2$-cyanoguanidino)phenyl]-5-methyl-4,5-dihydro-3(2H)-pyridazinone,
and pharmaceutically acceptable salts thereof.

The compounds of the invention are depicted as dihydropyridazin-3(2H)-ones, but of course the present invention covers all tautomeric forms thereof, for example the dihydropyridazinol form and all the tautomeric forms of the —NH—C(=NR³)NHR² group.

Furthermore the present invention covers all the optical isomeric forms of the compounds of the formula (I) in the racemic and separated forms. In particular when R¹ is methyl the (R) isomers of the compounds of the formula (I) (vide infra) are preferred.

Compounds of the formula (I) may form pharmaceutically acceptable salts with metal ions, such as alkali metals for example sodium and potassium, or alkaline earth metals for example calcium and magnesium.

In order to use a compound of the formula (I) or a pharmaceutically acceptable salt thereof for the treatment of humans and other mammals it is normally formulated in accordance with standard pharmaceutical practice as a pharmaceutical composition.

Compounds of formula (I) and their pharmaceutically acceptable salts may be administered in standard manner for the treatment of the indicated diseases, for example orally, parenterally, trans-dermally, rectally, via inhalation or via buccal administration.

Compounds of formula (I) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (I) or a pharmaceutically acceptable salt thereof which is active when administered in this way, with a binding and/or lubricating agent, for example polymeric glycols, gelatins, cocoa-butter or other low melting vegetable waxes or fats.

Typical transdermal formulations comprise of a conventional aqueous or non-aqueous vehicle, for example a cream, ointment, lotion or paste or in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example a tablet, capsule or metered aerosol dose, so that the patient may administer to himself a single dose.

Each dosage unit for oral administration contains suitably from 0.01 mg/Kg to 3 mg/Kg, and preferably from 0.05 mg/Kg to 1.5 mg/Kg, and each dosage unit for parenteral administration contains suitably from 0.001 mg/Kg to 1 mg/Kg, of a compound of formula (I) or a pharmaceutically acceptable salt thereof calculated as the free base.

The daily dosage regimen for oral administration is suitably about 0.01 mg/Kg to 12 mg/Kg, of a compound of formula (I) or a pharmaceutically acceptable salt thereof calculated as the free base. The daily dosage regimen for parenteral administration is suitably about 0.001 mg/Kg to 4 mg/Kg, for example about 0.01 mg/Kg to 1 mg/Kg, of a compound of the formula (I) or a pharmaceutically acceptable salt thereof calculated as the free base. The active ingredient may be administered from 1 to 4 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure. The compounds of the invention are also bronchodilators and are useful in chronic obstructive lung disease for example asthma and bronchitis. Such conditions can be treated by administration orally, rectally, parenterally or by inhalation. For administration by inhalation dosages are controlled by a valve, are administered as required and for an adult are conveniently in the range 0.1–5.0 mg of a compound of the formula (I) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (I) or pharmaceutically acceptable salts thereof, may be prepared by a process which comprises:

(a) reacting a compound of the formula (II):

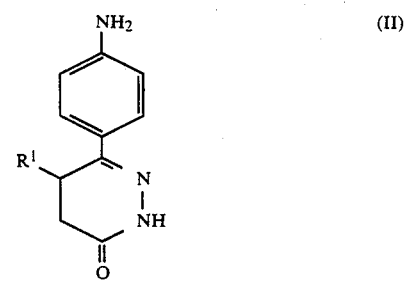

wherein R¹ is as hereinbefore defined, with a compound of the formula (III):

(III)

wherein $L^1$ is a leaving group, $R^3$ is as hereinbefore defined and R is a group $-NHR^2$ wherein $R^2$ is as hereinbefore defined or R is a leaving group $L^2$; and thereafter if R is a leaving group $L^2$ reacting with an amine $NH_2R^2$ wherein $R^2$ is as hereinbefore defined; or
(b) reacting a compound of the formula (IV):

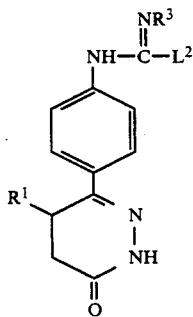

(IV)

with an amine $NH_2R^2$, wherein $L^2$, $R^1$, $R^2$ and $R^3$ are as hereinbefore defined; or
(c) reacting a compound of the formula (V):

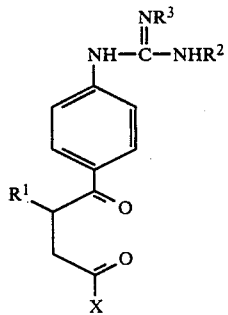

(V)

wherein $R^1$, $R^2$ and $R^3$ are as hereinbefore defined and X is a displaceable group, with hydrazine or a chemical equivalent thereof; or
(d) reacting a compound of the formula (VI):

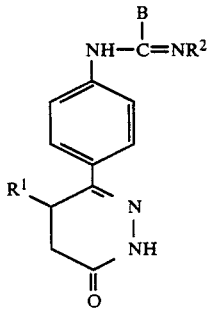

(VI)

wherein $R^1$ and $R^2$ are as hereinbefore defined, and B is a displaceable group, with a reagent $H_2NR^3$ wherein $R^3$ is as hereinbefore defined;

and thereafter optionally forming a pharmaceutically acceptable salt.

In the reaction between the compounds of the formulae (II) and (III), R can be a group $-NHR^2$ so that a compound of the formula (I) is formed directly. In a preferred alternative R is a leaving group $L^2$ which may be the same as, or different to, the leaving group $L^1$. Suitably $L^1$ and $L^2$ are both benzylthio or $C_{1-6}$alkylthio, for example they are preferably both methylthio. Such a reaction is conveniently performed in a solvent such as pyridine at an elevated temperature for example reflux. Suitably also $L^1$ and $L^2$ are each selected from $C_{1-6}$alkoxy, phenoxy or benzyloxy, preferably both $L^1$ and $L^2$ are phenoxy. Such a reaction is conveniently performed in an aprotic organic solvent such as dimethylformamide, or a $C_{1-4}$alkanol for example ethanol, at an elevated temperature, for example between 50° C. and 150° C., preferably between 100°-130° C.

When $L^1$ and $L^2$ are leaving groups the reaction of the compounds of the formulae (II) and (III) affords the compound of the formula (IV). This can be isolated and reacted, or reacted in situ, with an amine $R^2 NH_2$. Suitably such a reaction can be performed in a $C_{1-4}$-alkanol, for example ethanol, at an elevated temperature for example between 50° C. and reflux, that is about 79° C. for ethanol. Suitable and preferred leaving groups $L^2$ for formula (IV) are the same as for formula (III). Optionally the displacement of a leaving group $L^2$ can be performed in the presence of a salt of a heavy metal, in particular when $L^2$ is alkylthio. Suitably salts of heavy metals include salts of silver, mercury, cadmium or lead, preferably silver nitrate or mercuric chloride. In such cases the reaction is preferably performed in the presence of a base for example potassium carbonate.

The reaction between a compound of the formula (V) and hydrazine or a chemical equivalent thereof is suitably performed at ambient or elevated temperature, for example 15° C.-120° C., preferably about 30° C.-80° C. or at reflux temperature of a suitable solvent. The reaction is conveniently performed in a solvent such as water, a $C_{1-4}$alkanol for example methanol, ethanol or n-propanol, or aqueous or glacial acetic acid. Suitably in the compounds of the formula (V) X is hydroxy, $C_{1-6}$alkoxy, amino or $C_{1-6}$alkylamino.

In the reaction of a compound of the formula (VI) and $H_2NR^3$ or a salt thereof, B can be $C_{1-4}$alkylthio, mercapto, $C_{1-4}$alkoxy, phenoxy or benzyloxy. Preferably B is $C_{1-4}$alkylthio. Conveniently such reactions can be carried out in a $C_{1-4}$alkanol or dimethylformamide. The reactions of the compound of formula (VI) with $H_2NR^3$ may be carried out in the presence of a strong base for example those having anions of weak nucleophilic character such as sodium hydride or potassium t-butoxide. Suitably the reaction is carried out in a solvent under anhydrous conditions and preferably at an elevated temperature for example 60° C.-120° C., conveniently at the reflux temperature of a $C_{1-4}$alkanol. When potassium t-butoxide is the strong base it is convenient to use t-butanol as solvent.

The compounds of the formula (II) are known from Curran et al., J. Medicinal Chemistry, 17, p 273 (1974) and from European Patent Application 0150937.

The (R) and (S) isomers (respectively the (−) and (+) isomers) of the compound of the formula (II) wherein $R^1$ is methyl can be separated by passage of racemic compound over a chiral phase chromatography column. The appropriate fractions are collected, rechromatographed as necessary, solvent is evaporated and the desired isomer isolated in conventional manner.

The resolved form of a compound of the formula (I) can be prepared by reaction of the corresponding resolved form of a compound of formula (II) with a compound of the formula (III) in an analogous manner to the reaction of a compound of the formula (II) with a compound of formula (III) as hereinbefore described.

The compounds of the formula (V) can be prepared by reacting a compound of the formula (VII):

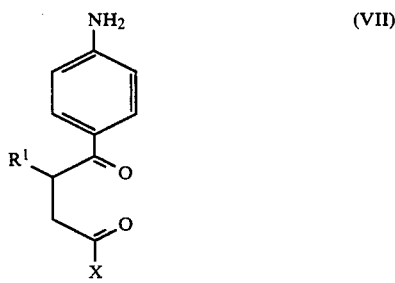

wherein R¹ and X are as hereinbefore defined, with a compound of the formula (III) as hereinbefore defined; in an analogous manner to that described for reacting compounds of the formulae (II) and (III). The compounds of the formula (VII) are known, or preparable in conventional manner, from the above-mentioned J. Medicinal Chemistry reference.

The compounds of the formula (VI) are known from EP-A-No. 84250 or can be prepared in conventional manner.

Pharmaceutically acceptable base addition salts of the compounds of the formula (I) may be prepared by standard methods, for example by reacting a solution of the compound of the formula (I) with a solution of the base.

The preparation of compounds of the formula (I) in general is summarised in the following scheme.

SCHEME

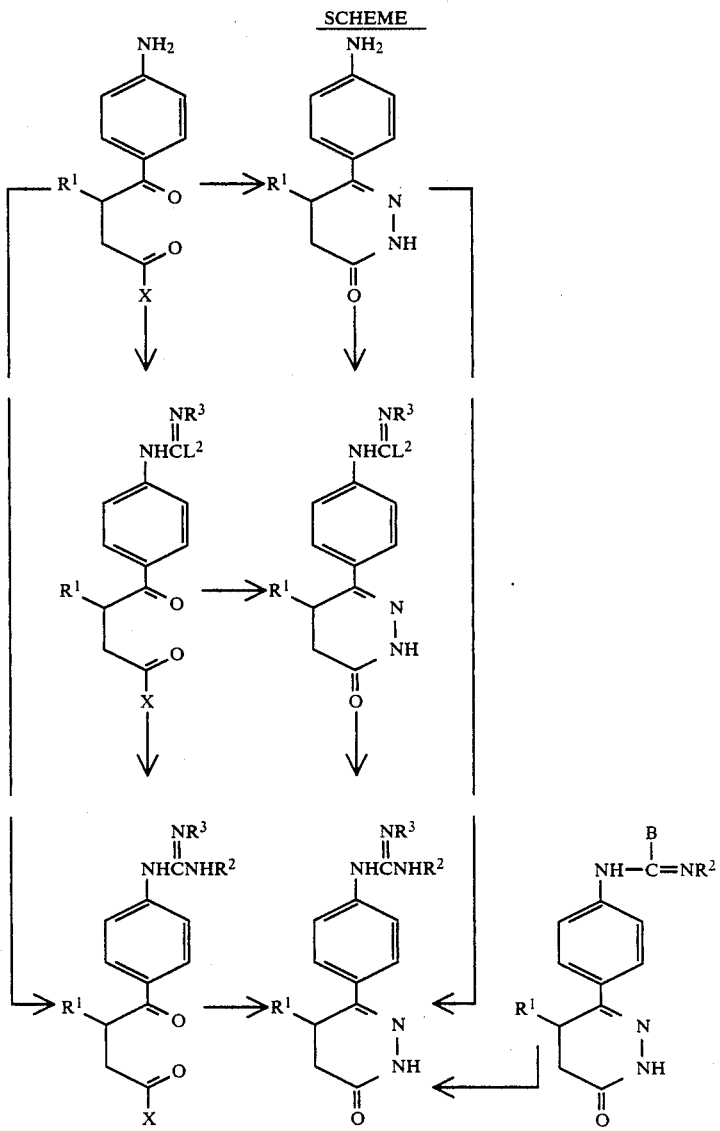

R¹, R², R³, L², B and X as defined in the text.

The following biological test methods and data serve to illustrate this invention.

Cardiac Stimulant Activity—In vitro

The compounds of formula (I) and their pharmaceutically acceptable salts are tested for cardiac stimulant activity following a procedure based on that of S. C. Verma and J. H. McNeill (J.Pharm & Exp. Therapeutics, 200, 352-362 (1977)). Guinea pigs (500-700 g) of either sex are sacrificed and the hearts are quickly removed and transferred to a dissecting dish containing oxygenated bathing fluid. While in the bathing medium, the right ventricle is cut into two strips. The strips are each suspended in a 50 ml bath containing Krebs Henseleit solution at 37° C., and the bath is bubbled with 95% oxygen and 5% carbon dioxide. The ventricular strips are electrically stimulated at a frequency of 1.0 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested gave a 50% increase in the force of contraction of the ventricular strips at concentrations in the bathing fluid of less than $10^{-4}$ molar, thus showing that they have activity as positive inotropic agents.

In the above test method the compounds of the Examples gave the following data:

| Compound of Example | $EC_{50} \times 10^{-6} M$ |
|---|---|
| 1 | 16 |
| 4 | 2.8 |
| 5 | 8 |
| 6 | 10 |
| 7 | 10 |
| 8 | 18 |
| 10 | 0.8 |
| 12 | 12 |
| 13 | 12.5 |
| Amrinone | 15 |

Cardiac Stimulant Activity—In vivo (Anaesthetised Cats)

In anaesthetised cats pretreated with a ganglion blocker (mecamylamine or pempidine) and propranolol, the compounds of the Examples cause sustained increases in left ventricular dp/dt max (this is an index of left ventricular contractility) when administered intravenously. The dose to increase left ventricular dp/dt max by 50% is given as the $ED_{50}$.

| Compound of Example | $ED_{50}$ (micromol/kg) | Relative # Duration |
|---|---|---|
| 1 | 0.5 | * |
| 2 | 0.2 | *** |
| 3 | 0.1 | ** |
| 4 | 0.2 | ** |
| 5 | 0.7 | *** |
| 6 | 0.4 | * |
| 7 | 0.3 | * |
| 8 | 0.4 | * |
| 9 | 0.4 | *** |
| 10 | 0.1 | *** |
| 11 | 0.5 | ** |
| Amrinone | 5.6 | * |

Relative duration was estimated in the anaesthetised cats following the i.v. administration:
***long:
**medium:
*short Minimal changes in blood pressure or heart rate were observed.

Inhibition of Phosphodiesterases

Three peaks of cyclic nucleotide phosphodiesterase activity [PDE (Peak I), PDE (Peak II) and PDE (Peak III)] from cat heart were separated by chromatography on DEAE-Sepharose CL-6B (Diethylaminoethyl Cellulose with a bead size of 45–165 microns). Sepharose is a registered trademark of Pharmacia Fine Chemicals Inc. The high-speed supernatant from a cat heart homogenate (2 g tissue in 20 ml 20 mM PIPES (Piperazine-N-N'-bis[2-ethanesulfonic acid]), 50 mM Na acetate, pH 6.5) was applied to a 15×1.5 cm column of DEAE-Sepharose equilibrated with the homogenisation buffer. The PDE activities were eluted with a gradient of 0.05–1M Na acetate in 20 mM PIPES. There were three major peaks which had the following characteristics:

PDE (Peak I)—eluted at 0.15M Na acetate

| | PDE (Peak I) - eluted at 0.15 M Na acetate | | |
|---|---|---|---|
| Substrate | 50 μg/ml calmodulin (+ = added) | Km (μM) | Relative $V_{max}$ |
| cyclic AMP | − | 0.5 | 1 |
| cyclic GMP | − | 1.8 | 1.1 |
| cyclic AMP | + | 0.7 | 6.3 |
| cyclic GMP | + | 1.4 | 7.2 |

PDE (Peak II)—eluted at 0.03M Na acetate

| PDE (Peak II) - eluted at 0.3 M Na acetate | | |
|---|---|---|
| Substrate | Km (μM) | Relative $V_{max}$ |
| cyclic AMP | 6 | 1 |
| cyclic GMP | 28 | 0.2 |

PDE (Peak III)—eluted at 0.5M Na acetate

| PDE (Peak III) - eluted at 0.5 M Na acetate | | |
|---|---|---|
| Substrate | Km (μM) | Relative $V_{max}$ |
| cyclic AMP | 0.6 | 1 |
| cyclic GMP | 2.9 | 0.4 |

PDE (Peak I) has high affinity for cyclic AMP and cyclic GMP and is characterised by an activation by $Ca^{2+}$/calmodulin complex.

PDE (Peak II) demonstrates relatively low affinities for both cyclic AMP and cyclic GMP and is not affected by $Ca^{2+}$/calmodulin complex.

PDE (Peak III) has high affinity for cyclic AMP. It can also hydrolyse cyclic GMP though the preferred substrate is cyclic AMP. This activity is also insensitive to $Ca^{2+}$/calmodulin activation.

Enzyme assay

The enzyme was assayed by incubation at 37° for 4–30 min in 50 mM Tris, 5 mM $MgCl_2$, pH 7.5 with [3-H] cyclic nucleotide ($4 \times 10^5$ disintegrations min$^{-1}$) and [14-C] nucleotide 5' monophosphate ($3 \times 10^3$ disintegrations min$^{-1}$). The assay was stopped by boiling, and the [3-H] 5' monophosphate product separated from substrate on boronate columns (Davis, C. W. and Daly, J. W. (1979) J. Cyclic Nucleotide Res., 5, 65–74). The reaction mixture was diluted with 0.5 ml 100 mM HEPES (N-2-Hydroxyethylpiperazine-N'-2-ethanesulfonic acid), 100 mM NaCl, pH 8.5, and applied to the column. The column was extensively washed with the same buffer, and the 5' nucleotide eluted with 6 ml 0.25M acetic acid. The recovery of product as judged by [14-C] recovery was approximately 80%. All assays were linear with time of incubation and concentration of enzyme over the range used in these experiments.

Calculation of $IC_{50}$ values $IC_{50}$ values (the concentration of inhibitor required for 50% inhibition of activity) were obtained for PDE (Peak III) by incubation of the enzymes at 1 μM cyclic AMP, and a range of inhibitor concentrations from $0.1 \times IC_{50}$ to $100 \times IC_{50}$.

| Compound of Example | $IC_{50} \times 10^{-6}$M |
| --- | --- |
| 1 | 2.23 |
| 2 | 2.48 |
| 3 | 0.23 |
| 9 | 0.08 |
| Amrinone | 51.8 |
| Milrinone | 2.2 |

Vasodilator Activity

The compounds of the Examples were tested in autoperfused anaesthetised cat hind quarters (autoperfused at constant blood flow). The dose to decrease hindquarters perfusion pressure (vasodilatation) by 15% is given as the $ED_{15}$.

| Compound of Example | $ED_{15}$ (μm/kg) |
| --- | --- |
| 1 | 0.61 |
| 2 | 0.18 |
| 3 | 0.08 |
| 6 | 0.32 |
| 9 | 0.69 |

The invention is illustrated and in no way limited by the following Description and Examples.

DESCRIPTION 1

(+) and
(−)-6-(4-Aminophenyl)-5-methyl-4,5-dihydro-3(2H)-pyridazinone

Racemic 6-(4-aminophenyl)-5-methyl-4,5-dihydro-3(2H)-pyridazinone (2.0 g) dissolved in a mixture of acetonitrile (80 ml) and dichloromethane (30 ml) was added to a column of ionically bound (R)-N-(3,5-dinitrobenzoylphenyl)glycine on 40 μm α-aminopropyl silanized silica (2.1 kg), packed at 1104 kPa (160 p.s.i.) (by slurrying with dichloromethane (1.5 L)) in a Jobin-Yvon medium pressure liquid chromatography system. The column was eluted with dichloromethane/methanol (199:1) over 9 hours at a rate of 80 ml min$^{-1}$. Detection was by u.v. at 280 nm. A broad peak was obtained from which fractions were collected. The earlier fractions were enriched (−) enantiomer. These fractions were combined and re-chromatographed through the same column with the same eluant.

The selected column fractions were evaporated, triturated with diethyl ether, filtered and the resultant solid washed with diethyl ether and dried at 80° C. for 18 hours to give (−)-6-(4-aminophenyl)-5-methyl-4,5-dihydro-3(2H)-pyridazinone, in approximately 100% enantiomeric excess, m.p. 203°–204° C.; $[\alpha]_D^{25} = -399°$ [concentration 0.74% in ethanol:water:conc. HCl (17:2:1)].

A sample of the (−) isomer was reacted with 3-bromopropionyl chloride to afford enantiomerically pure (−)-6-[4-(3-bromopropionamido)phenyl]-5-methyl-4,5-dihydro-3(2H)-pyridazinone, the absolute configuration of which was shown by a X-ray diffraction study to be (R).

The later fractions from the first column were enriched (+) enantiomer (approximately 75% enrichment) which was subjected to medium pressure liquid chromatography (Jobin-Yvon system) over a column of ionically bound (S)-N-(3,5-dinitrobenzoyl)phenylglycine on 25–40 μm α-aminopropyl silanized silica (55 g) eluting with dichloromethane/methanol (199:1). The appropriate fractions were combined with fractions from another run and re-chromatographed through the same column.

The selected column fractions were evaporated, triturated with diethyl ether, filtered and the resultant solid washed with diethyl ether and dried at 80° C. for 18 hours to give (+)-6-(4-aminophenyl)-5-methyl-4,5-dihydro-3(2H)-pyridazinone, in approximately 100% enantiomeric excess, m.p. 206°–208° C.; $[\alpha]_D^{25} = +376°$ [concentration 0.74% in ethanol:water:conc. HCl (17:2:1)].

EXAMPLE 1

6-[4-(N$^2$-acetylguanidino)phenyl]-5-methyl-4,5-dihydro-3(2H)-pyridazinone

A stirred mixture of 6-(4-aminophenyl)-5-methyl-4,5-dihydro-3(2H)-pyridazinone, (1.0 g) N-acetyl-S-methylisothiourea hydroiodide (1.34 g) and pyridine (10 ml) was heated under reflux for 30 minutes. The residue after evaporation was dissolved in water (10 ml) and potassium carbonate was added to pH 9–10 to give a solid (1.14 g), m.p. ca 225°–230° C. dec. Material from several reactions was combined and recrystallised from aqueous ethanol to give the title compound in 63% recovery, m.p. ca 240° C. dec., (dimethylsulphoxide-d$_6$, 360 MHz); 1.08 (d, CH$_3$), 2.08 (s, COCH$_3$), 2.23, 2.65 (m, CH$_2$), 3.37 (m, CHCH$_3$); 7.08, 7.70 (m, aromatic); ca 7.2 (br, guanidino NH, NH$_2$); 10.78 (s, pyridazinone NH).

EXAMPLE 2

6-[4-(N$^3$-methyl-N$^2$-methylsulphonylguanidino)-phenyl]-5-methyl-4,5-dihydro-3(2H)-pyridazinone A stirred mixture of 6-(4-aminophenyl)-5-methyl-4,5-dihydro-3(2H)-pyridazinone (3.5 g), dimethyl-N-(methylsulphonyl)dithioiminocarbonate (5.14 g) and pyridine (40 ml) was heated under reflux for 6 hours. Evaporation gave crude 6-(4-(N-methylsulphonyl-S-methylisothioureido)phenyl)-5-methyl-4,5-dihydro-3(2H)-pyridazinone which was dissolved in 33% methylamine in ethanol (50 ml) and the solution was heated under reflux for 1½ hours. The residue left after evaporation was dissolved in dichloromethane (50 ml) and the solution was washed with dilute hydrochloric acid and water. Evaporation gave the crude product as a solid, 1.79 g, 31%. Column chromatography (silica gel, chloroform:methanol 25:1) and recrystallisation from acetonitrile gave the partly purified title compound, 1.0 g, 17% m.p. 228°–230° C. Further purification by medium pressure liquid chromatography (silica gel, chloroform:methanol; 100:0, 99:1) and recrystallisation from aqueous ethanol gave the pure title compound, m.p. 235°–237° C.

EXAMPLE 3

6-[4-($N^3$-methyl-$N^2$-phenylsulphonylguanidino)phenyl]-5-methyl-4,5-dihydro-3(2H)-pyridazinone A stirred mixture of 6-(4-aminophenyl)-5-methyl-4,5-dihydro-3(2H)-pyridazinone (2.96 g), and dimethyl-N-(phenylsulphonyl)dithioiminocarbonate (3.92 g) in dry pyridine (40 ml) was heated under reflux for 5 hours and then evaporated under reduced pressure. A solution of the residue in chloroform (50 ml) was treated with hydrochloric acid (1N, 25 ml), the solid removed by filtration, and the organic solution was washed with water, dried, and evaporated onto silica gel. Medium pressure chromatography (silica gel:chloroform) gave the intermediate 5-methyl-6-[4-N-(phenylsulphonyl-S-methylisothioureido)phenyl]-4,5-dihydro-3(2H)-pyridazinone (1.87 g, m.p. 199°–201° C.) which was collected from ether.

A solution of the intermediate in 33% ethanolic methylamine (30 ml) was heated under reflux for 45 minutes. Trituration of the cold mixture gave the crude product, 1.69 g, m.p. 235°–236° C. Recrystallisation from ethanol gave the pure title compound, 1.25 g, m.p. 241°–242° C.

EXAMPLE 4

6-[4-($N^3$-(2-Methoxyethyl)-$N^2$-cyanoguanidino)phenyl]-5-methyl-4,5-dihydro-3(2H)-pyridazinone (i) A solution of 6-(4-aminophenyl)-5-methyl-4,5-dihydro-3(2H)-pyridazinone (2.0 g, 0.0098 mol) and diphenyl cyanoiminocarbonate (2.4 g, 0.01 mol), in anhydrous dimethylformamide (15 ml) was stirred at 115°–120° C. for 6 hours. Further diphenyl cyanoiminocarbonate (0.6 g, 0.0025 mol) was then added and the solution heated for a further 2 hours. Evaporation of the solvent under reduced pressure gave a brown residue which was washed with boiling ethanol and then recrystallised from aqueous dimethylformamide to give 6-[4-[($N^2$-cyano)phenoxyformamidino]phenyl]-5-methyl-4,5-dihydro-3(2H)-pyridazinone, 1.5 g, m.p. 164°–165° C. This can also be recrystallised from acetonitrile.

(ii) A stirred mixture of the above formamidine (2 g, 0.0043 mol), 2-methoxyethylamine (1.5 ml) and ethanol (100 ml) was heated under reflux for 2.5 hours. After evaporation the crude product was collected from ethanol and purified by flash chromatography (silica, chloroform: methanol mixtures) to give the title compound (1.15 g), m.p. 196°–197° C.

EXAMPLE 5

6-[4-($N^3$-(2-Hydroxyethyl)-$N^2$-cyanoguanidino)phenyl]-5-methyl-4,5-dihydro-3(2H)-pyridazinone (i) To 6-(4-aminophenyl)-5-methyl-4,5-dihydro-3(2H)-pyridazinone (4 g) in anhydrous pyridine (25 ml) was added dimethyl cyanodithioiminocarbonate (5.75 g) and the mixture was stirred under reflux for 3 hours. The reaction mixture was evaporated under reduced pressure to approximately half volume, diluted with ethanol and allowed to stand to afford a solid (3.85 g). The filtrate on standing and on trituration yielded further solid (1.42 g). The solids were combined and dissolved in boiling pyridine (60 ml) containing a little water. The solution was filtered and reduced in volume to give a slurry which was diluted with acetone and left to stand. This afforded crystals of 6-(4-(N-cyano-S-methylisothioureido)phenyl)-5-methyl-4,5-dihydro-3(2H)-pyridazinone, (4.02 g), m.p. 231°–232° C. (decomp.)

(ii) A stirred mixture of 6-(4-(N-cyano-S-methylisothioureido)phenyl)-5-methyl-4,5-dihydro-3(2H)-pyridazinone (1 g), ethanolamine (2 ml) and ethanol (20 ml) was heated under reflux for 45 minutes. The residual oil after evaporation was stirred with water (10 ml) and acetic acid was added to pH 4 to give 0.75 g of a solid, m.p. 202°–203° C. dec. A total of 1.12 g of this solid was recrystallised from aqueous methanol to give the title compound (0.79 g), m.p. 205.5°–207° C. dec.

EXAMPLE 6

6-[4-($N^3$-Cyclopropyl)-$N^2$-cyanoguanidino)phenyl]-5-methyl-4,5-dihydro-3(2H)-pyridazinone A stirred mixture of 6-(4-(N-cyano-S-methylisothioureido)phenyl)-5-methyl-4,5-dihydro-3(2H)-pyridazinone (1 g), cyclopropylamine (3 ml), ethanol (20 ml) and pyridine (4 ml) was heated under reflux for 2 hours. Sufficient water was added to the resultant mixture to give a solution which was treated with charcoal, filtered, and evaporated to reduced volume. The residue was diluted with ethanol to give a solid, (0.88 g, 85%) m.p. 242°–243.5° C. The products from two reactions were combined and recrystallised from aqueous ethanol to give the title compound in 85% recovery, m.p. 243°–244.5° C.

EXAMPLE 7

6-[4-($N^3$-Allyl-$N^2$-cyanoguanidino)phenyl]-5-methyl-4,5-dihydro-3(2H)-pyridazinone A solution of 6-[4-[($N^2$-cyano)phenoxyformamidino]phenyl]-5-methyl-4,5-dihydro-3(2H)-pyridazinone (1.5 g) and allylamine (2.6 g) in ethanol 50 ml) was stirred under reflux for 2 hours. The resultant suspension was allowed to stand at room temperature to afford a yellow precipitate (1.07 g) which was taken up in boiling acetonitrile (200 ml). The solution was treated with charcoal, filtered and evaporated to reduced volume to give a slurry which was left to stand at 0° C. This afforded white crystals of the title compound (0.55 g), m.p. 224°–226° C.

EXAMPLE 8

6-[4-($N^3$-Propargyl-$N^2$-cyanoguanidino)phenyl]-5-methyl-4,5-dihydro-3(2H)-pyridazinone A solution of 6-[4-[($N^2$-cyano)phenoxyformamidino]phenyl]-5-methyl-4,5-dihydro-3(2H)-pyridazinone (2.0 g) and propargylamine (0.5 g) in ethanol (100 ml) was stirred under reflux for 2 hours. Further propargylamine (0.5 g) was added and the mixture was stirred under reflux for one hour. The reaction mixture was evaporated under reduced pressure and the residual brown oil was subjected to 'flash' column chromatography on silica (chloroform: methanol; 100:1, 60:1 and 50:1 as eluant). The desired fractions were combined and evaporated under reduced pressure to give a pale yellow solid (0.35 g), which was recrystallised from acetonitrile to afford the title compound (0.14 g), m.p. 200°–290° C. (slow dec.). γ(nujol); 3400–2600, 2175, 2120, 1668, 1610, 1595, 1560 cm$^{-1}$, δ(DMSO-d$_6$); inter alia 1.10 (3H, d, CH$_3$CH), 3.14 (1H, t, —C≡CH), 4.04 (2H, d, —CH$_2$C≡CH).

EXAMPLE 9

6-[4-(N$^3$-(4-Hydroxybenzyl)-N$^2$-cyanoguanidino)-phenyl]-5-methyl-4,5-dihydro-3(2H)-pyridazinone A stirred mixture of 6-[4-[(N$^2$-cyano)phenoxyformamidino]phenyl]-5-methyl-4,5-dihydro-3(2H)-pyridazinone (2 g,) and a solution of 4-hydroxybenzylamine (1 g) and ethanol (100 ml) was heated under reflux for 3.5 hours to give a solid (1.5 g, m.p. 240°–242° C.). This was digested with hot ethanolic chloroform and the digest treated with charcoal and evaporated. The residue was collected from ethanol to give the title compound (0.43 g), m.p. 248°–252° C. (dec.).

EXAMPLE 10

6-[4-(N$^3$-Benzyl-N$^2$-cyanoguanidino)phenyl]-5-methyl-4,5-dihydro-3(2H)-pyridazinone A stirred mixture of 6-(4-(N-cyano-S-methylisothioureido)phenyl)-5-methyl-4,5-dihydro-3(2H)-pyridazinone (2 g), benzylamine (2 ml) and pyridine (100 ml) was heated under reflux for 2 hours. The residue after evaporation was triturated with ethanol and the resultant solid (1.6 g) was purified by flash chromatography (silica gel, chloroform:methanol mixtures) to give the title compound (0.85 g), m.p. 228°–229° C.

EXAMPLE 11

6-[4-(N$^3$-(4-Methoxybenzyl)-N$^2$-cyanoguanidino)-phenyl]-5-methyl-4,5-dihydro-3(2H)-pyridazinone In a manner similar to that of Example 10, reaction of 6-(4-(N-cyano-S-methylisothioureido)phenyl)-5-methyl-4,5-dihydro-3(2H)-pyridazinone (2 g) with 4-methoxybenzylamine (3 g) gave a crude product (1.9 g) which was digested with hot ethanol to leave the title compound (1.4 g); m.p. 231°–233° C.

EXAMPLE 12

6-[4-(N$^3$-(2-Pyridylmethyl)-N$^2$-cyanoguanidino)-phenyl]-5-methyl-4,5-dihydro-3(2H)-pyridazinone In a manner similar to that of Example 10, reaction of 6-(4-(N-cyano-S-methylisothioureido)phenyl)-5-methyl-4,5-dihydro-3(2H)-pyridazinone (2 g) with 2-(aminomethyl)pyridine (2.6 g) gave an oil which was dissolved in hot chloroform and the solution allowed to stand to give 0.6 g of a solid. Recrystallisation from acetonitrile gave the title compound (0.12 g) while column chromatographic purification of the filtrate and mother liquor (silica gel, chloroform:methanol mixtures) gave a further 0.18 g, m.p. 212°–214° C. (from dichloromethane).

EXAMPLE 13

6-[4-(N$^3$-Phenethyl-N$^2$-cyanoguanidino)phenyl]-5-methyl-4,5-dihydro-3(2H)-pyridazinone A stirred mixture of 6-(4-(N-cyano-S-methylisothioureido)phenyl)-5-methyl-4,5-dihydro-3(2H)-pyridazinone, (2 g), phenethylamine (8.4 ml) and pyridine (40 ml) was heated under reflux for 3 hours. The mixture was evaporated under reduced pressure to yield an oil, which on trituration with one normal acetic acid (17 ml) gave 1.1 g of a solid, m.p. 209°–210° C. Recrystallisation from ethanol gave the pure title compound, 0.64 g, m.p. 215°–217° C.

EXAMPLE 14

(R)-6-[4-(N$^3$-Benzyl-N$^2$-cyanoguanidino)phenyl]-5-methyl-4,5-dihydro-3(2H)-pyridazinone (i) A stirred mixture of (R)-6-(4-aminophenyl)-5-methyl-4,5-dihydro-3(2H)-pyridazinone (4 g) and dimethyl cyanodithioiminocarbonate in pyridine is heated to afford (R)-6-(4-(N-cyano-S-methylisothioureido)-phenyl)-5-methyl-4,5-dihydro-3(2H)-pyridazinone.

(ii) A stirred mixture of (R)-6-(4-(N-cyano-S-methylisothioureido)phenyl)-5-methyl-4,5-dihydro-3(2H)-pyridazinone and benzylamine in pyridine is heated to afford (R)-6-[4-(N$^3$-benzyl-N$^2$-cyanoguanidino)phenyl]-5-methyl-4,5-dihydro-3(2H)-pyridazinone.

EXAMPLE 15

N$^1$-[4-(3-Ethoxycarbonyl-2-methylpropionyl)phenyl]-N$^3$-benzyl-N$^2$-cyanoguanidine A mixture of diphenyl cyanoiminocarbonate and ethyl 3-(4-aminobenzoyl)butyrate in dimethylformamide is heated to afford N$^1$-[4-(3-ethoxycarbonyl-2-methylpropionyl)-phenyl]-(N$^2$-cyano)phenoxyformamidine. This compound is reacted with benzylamine in ethanol with heating and stirring to afford the title compound.

EXAMPLE 16

Pharmaceutical compositions for oral administration are prepared by combining the following:

|  | % w/w | | |
|---|---|---|---|
| 6-[4-(N$^3$-methyl-N$^2$-methyl sulphonylguanidino)phenyl]-4,5-dihydro-5-methyl-3(2H)-pyridazinone | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 17

A pharmaceutical composition for parenteral administration is prepared by dissolving the title compound of Example 10 (0.02 g) in polyethylene glycol 300 (25 ml) with heating. This solution is then diluted with water for injections E.P. (to 100 ml). The solution is then sterilised by filtration through a 0.22 micron membrane filter and sealed in sterile containers.

Compositions containing the compound of Example 10 (0.04 g) in polyethylene glycol 300 are prepared in analogous manner.

What is claimed is:

1. A compound of the formula (I):

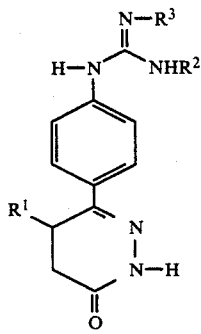

(I)

or a pharmaceutically acceptable salt thereof wherein:
$R^1$ is hydrogen or methyl;
$R^2$ is $C_{1-4}$ alkyl, or $C_{1-4}$ alkyl substituted by on or two groups selected from hydroxy, $C_{1-4}$ alkoxy, carbamoyl, $C_{1-4}$ alkoxycarbonyl and trifluoromethyl, provided that the carbon atom adjacent to the nitrogen atom is not substituted by hydroxy and that no carbon atom is distributed by hydroxy, or —A—$R^4$ where A is $C_{1-4}$ alkylene (straight or branched) and $R^4$ is phenyl or phenyl substituted by one or two alkoxy, halo, hydroxy, sulfonamido, or trifluoromethyl groups, or is 2-, 3- or 4- pyridyl or 2-benzimidazolyl;
$R^3$ is cyano, $COR^5$ or $-SO_2R^6$ where $R^5$ is $C_{1-4}$ alkyl, $C_{1-4}$ alkoxy or phenyl and $R^6$ is $NHR^7$, $C_{1-4}$ alkyl or phenyl; and $R^7$ is hydrogen or $C_{1-4}$ alkyl, $R^2$ can also be $C_{3-6}$ cycloalkyl, alkyl or propargyl when $R^3$ is cyano; provided that $R^2$ is not $C_{1-4}$ alkyl when $R_3$ is cyano.

2. A compound according to claim 1 wherein $R^1$ is methyl.

3. A compound according to claim 1 wherein $R^3$ is cyano.

4. A compound according to claim 1 wherein $R^3$ is acetayl, methylsulphonyl or phenylsulphonyl.

5. A compound according to claim 1 wherein $R^2$ is 2-hydroxyethyl or 2-methoxyethyl.

6. A compound according to claim 1 wherein A is $CH_2$ or $CH_2CH_2$.

7. A compound according to claim 1 wherein $R^4$ is phenyl or phenyl substituted by one or two $C_{1-4}$ alkoxy halo, hydroxy, sulphonamido or trifluoromethyl groups, or is a 2,3 or 4-pyridyl or 2-benzimidazoyl.

8. A compound according to claim 7 wherein $R^4$ is phenyl, 4-hydroxyphenyl or 2-pyridyl.

9. A compound according to claim 3 wherein $R^2$ is cyclopropyl, allyl or propargyl.

10. A compound according to claim 4 wherein $R^2$ is hydrogen or methyl.

11. A compound according to claim 1 which is:
6-[4-($N^2$-acetylguanidino)phenyl]-5-methyl-4,5-dihydro-(3(2H)-pyridazinone,
6-[4-($N^3$-methyl-$N^2$-methylsulphonylguanidino)-phenyl]-5-methyl-4,5-dihydro-3(2H)-pyridazinone,
6-[4-($N^3$-methyl-$N^2$-phenylsulphonylguanidino)-phenyl]-5-methyl-4,5-dihydro-3(2H)-pyridazinone,
6-[4-($N^3$-(2-methoxyethyl)-$N^2$-cyanoguanidino)-phenyl]-5-methyl-4,5-dihydro-3(2H)-pyridazinone,
6-[4-($N^3$-(2-hydroxyethyl)-$N^2$-cyanoguanidino)-phenyl]-5-methyl-4,5-dihydro-3(2H)-pyridazinone,
6-[4-($N^3$-cyclopropyl-$N^2$-cyanoguanidino)phenyl]-5-methyl-4,5-dihydro-3(2H)-pyridazinone,
6-[4-($N^3$-allyl-$N^2$-cyanoguanidino)phenyl]-5-methyl-4,5-dihydro-3(2H)-pyridazinone,
6-[4-($N^3$-propargyl-$N^2$-cyanoguanidino)phenyl]-5-methyl-4,5-dihydro-3(2H)-pyridazinone,
6-[4-($N^3$-(4-hydroxybenzyl)-$N^2$-cyanoguanidino)-phenyl]-5-methyl-4,5-dihydro-3(2H)-pyridazinone,
6-[4-($N^3$-benzyl-$N^2$-cyanoguanidino)phenyl]-5-methyl-4,5-dihydro-3(2H)-pyridazinone,
6-[4-($N^3$-(4-methoxybenzyl)-$N^2$-cyanoguanidino)-phenyl]-5-methyl-4,5-dihydro-3(2H)-pyridazinone,
6-[4-($N^3$ (2-pyridylmethyl)-$N^2$-cyanoguanidino)-phenyl]-5-methyl-4,5-dihydro-3(2H)-pyridazinone, or
6-[4-($N^3$-phenethyl-$N^2$-cyanoguanidino)phenyl]-5-methyl-4,5-dihydro-3(2H)-pyridazinone, or
or a pharmaceutically acceptable salt thereof.

12. A compound according to claim 1 which is:
6-[4-($N^3$-methyl-$N^2$-phenylsulphonylguanidino)-phenyl]-5-methyl-4,5-dihydro-3(2H)-pyridazinone, or a pharmaceutically acceptable salt thereof.

13. A compound according to claim 1 which is:
6-[4-($N^3$-benzyl-$N^2$-cyanoguanidino)phenyl]-5-methyl-4,5-dihydro-3(2H)-pyridazinone, or a pharmaceutically acceptable salt thereof.

14. A compound according to claim 2 in which the (R) isomer is enantiomerically enriched.

15. The (R) isomer of a compound according to claim 2.

16. A pharmaceutical composition having cardiac stimulating activity which comprises an effective amount therefor of a compound according to claim 1 and a pharmaceutically acceptable carrier.

17. A pharmaceutical composition having bronchodilator activity which comprises an effective amount therefor of a compound according to claim 1 and a pharmaceutically acceptable carrier.

18. A pharmaceutical composition having phosphodiesterase (type III) inhibition activity which comprises an effective amount therefor of a compound according to claim 1 and a pharmaceutically acceptable carrier.

19. A pharmaceutical composition according to claim 16 in unit dose form adapted for oral administration.

20. A compound of the formula (IV):

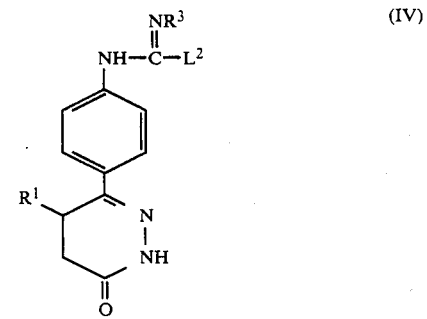

(IV)

wherein:
$R^1$ is hydrogen or methyl,
$R^3$ is $COR^5$ or $SO_2R^6$ where $R^5$ is $C_{1-4}$ alkyl, $C_{1-4}$ alkoxy or phenyl and $R^6$ is $NHR^7$, $C_{1-4}$ alkyl or phenyl; and $R^7$ is hydrogen or $C_{1-4}$ alkyl; and
$L^2$ is selected from the group consisting of benzylthio, $C_{1-6}$ alkylthio, $C_{1-6}$ alkoxy, phenoxy and benzyloxy.

* * * * *